United States Patent [19]

Kohler

[11] Patent Number: 4,962,909
[45] Date of Patent: Oct. 16, 1990

[54] MOLD FOR DENTISTRY

[76] Inventor: Wolfgang Kohler, Bahnhofsplatz 4, 8910 Landsberg, Fed. Rep. of Germany

[21] Appl. No.: 306,028
[22] PCT Filed: May 19, 1988
[86] PCT No.: PCT/DE88/00295
  § 371 Date: Jan. 12, 1989
  § 102(e) Date: Jan. 12, 1989
[87] PCT Pub. No.: WO88/09155
  PCT Pub. Date: Dec. 1, 1988

[30] Foreign Application Priority Data

May 20, 1987 [DE] Fed. Rep. of Germany ... 8707277[U]
Feb. 8, 1988 [DE] Fed. Rep. of Germany ... 8801580[U]

[51] Int. Cl.$^5$ .................................. A61C 13/20
[52] U.S. Cl. .................................. 249/54; 164/35;
  164/246; 164/DIG. 4; 249/62; 249/149;
  249/177; 264/19
[58] Field of Search ............ 249/54, 55, 57, 62,
  249/176, 177, 148, 149; 164/34-36, 246, DIG.
  4; 264/16, 19

[56] References Cited

U.S. PATENT DOCUMENTS 3,064,309 11/1962 Steinbock et al. ............ 164/35
3,698,468 10/1975 Hudson ............ 164/DIG. 4
3,768,544 10/1973 Padeh ............ 164/DIG. 4
3,985,178 10/1976 Cooper ............ 164/237
4,825,934 5/1989 Kai ............ 249/54

OTHER PUBLICATIONS

Das Zahnärztliche Und Zahntechnische Vorgehen Beim Teleskopsystem in Der Prothetik, of Professor Dr. Hermann Bottger and Zahn technikermeister Horst Grundler, 1978, pp. 119-134.

Primary Examiner—James C. Housel
Attorney, Agent, or Firm—Collard, Roe & Galgano

[57] ABSTRACT

A casting mold for the production of muffles which serve for the conversion of wax models to metal, with the casting mold having a funnel shaper (1) which consists of a disk-shaped base plate (4), at the circumference of which a side wall (5) which stands vertical to the base plate (4) runs, and a cone (6) arranged in the center of the base plate (4), pipe-shaped, muffle ring (2) partially inserted into the funnel shaper (1), with the outside wall of the muffle ring (2) resting against the inside circumference of the side wall (1) of the funnel shaper (1), a cylindrical ring (7) which is inserted on the side of the muffle ring (2) which faces the funnel shaper (1) and the central opening (8) of which surrounds the cone (6), and a blind funnel (3) provided on the side of the muffle ring (2) opposite the funnel shaper (3), whose funnel tip faces towards the cone (6) of the funnel shaper (1). In this manner, uniform, three-dimensional expansion of the embedding mass can be achieved in the area of the casting cavities.

17 Claims, 2 Drawing Sheets

MOLD FOR DENTISTRY

BACKGROUND OF THE INVENTION

1. Field of the Invention

The invention concerns a casting mold for the production of muffles for use in dental prosthetic manufacture.

2. The Prior Art

Such a casting mold is known from "Das zahnrztiche and zahntechnische Vorgehen beim Teleskopsystem in der Prosthetik", "Dental and Dental Surgery Procedures using the Telescope System in Prosthetics" by Bottger and Gründler, Verlag Neuer Merkur GmbH, Munich, 1978. In order to be able to produce precise casting objects, such as crowns, bridges, inlays, onlays, telescopes and similar items from precious metals, the object must first be modeled in wax or a self-polymerizate. The wax model is subsequently provided with a casting channel, which serves for subsequent injection of the melt. The other end of the casting channel is attached to a funnel shaper in the form of a rubber socket. Subsequently, a pipe-shaped muffle ring is inserted into a depression located in the rubber socket with one part, and this ring then surrounds the wax model. Then the embedding mass is introduced into the casting muffle, with setting expansion occurring when the embedding mass sets, predominantly in the axial direction, since expansion of the embedding mass in a radial direction is prevented by the muffle ring.

After setting or curing of the embedding mass, the funnel shaper is pulled off from the set embedding mass and the muffle ring. The set embedding mass is subsequently heated to a temperature of 200° C. with the muffle ring, in order to drive out the wax. After the wax has been driven off, the mold, i.e. the set embedding mass with the muffle ring, is placed in an oven and is heated until it has reached the temperature desired for subsequent casting, namely 700° C. During this heating, thermal expansion takes place. Since the setting expansion mentioned above and the thermal expansion mentioned now predominantly occur in an axial direction, a distortion of the casting cavity in an axial direction takes place, which results in fitting inaccuracies of the casting object. To eliminate these fitting inaccuracies, other cost-intensive work procedures are then necessary.

SUMMARY OF THE INVENTION

It is an object of the present invention to develop a casting mold for the production of muffles for use in dental prosthetic manufacture in such a way that predominant distortion of the mold or the muffle in an axial direction can be prevented, so that the casting object exactly corresponds to the wax model.

The above object is accomplished in accordance with the present invention, by providing a cylindrical ring which is inserted on the side of the muffle ring which faces the funnel shaper, which ring is removed after the embedding mass has set, and a blind cone is provided on the side of the muffle ring opposite the funnel shaper, expansion of the embedding mass in the area of the casting objects can also take place towards the inside, i.e. towards the center axis of the muffle ring and below the casting objects downwards towards the side facing the casting funnel, so that uniform, three-dimensional enlargement of the casting cavity takes place, and therefore unilateral distortion can be prevented. The expansion is massdependent and the cylindrical ring has the effect that the same amount of mass expands in the vertical, axial and transverse direction. This spatially uniform expansion is equalized by the contraction of the precious metal during the casting cooling process. This makes it possible to avoid cost-intensive reworking of the casting objects. Also, less embedding mass is needed for the mold and the muffle.

Since the blind funnel can also be positioned and fixed as desired in the frontal surface of the muffle ring, according to the invention, a distance which is essentially uniform can be achieved between the wax model and the blind funnel, so that later, approximately the same amount of embedding material will be found in the area of the casting objects. The exact positioning of the blind funnel can also be carried out with a relatively simple construction.

BRIEF DESCRIPTION OF THE DRAWINGS

Other objects and features of the present invention will become apparent from the following detailed description considered in connection with the accompanying drawing which discloses several embodiments of the present invention. It should be understood, however, that the drawing is designed for the purpose of illustration only and not as a definition of the limits of the invention.

In the drawing wherein similar reference characters denote similar elements throughout the several views.

DETAILED DESCRIPTION OF PREFERRED EMBODIMENTS

Figure 1:
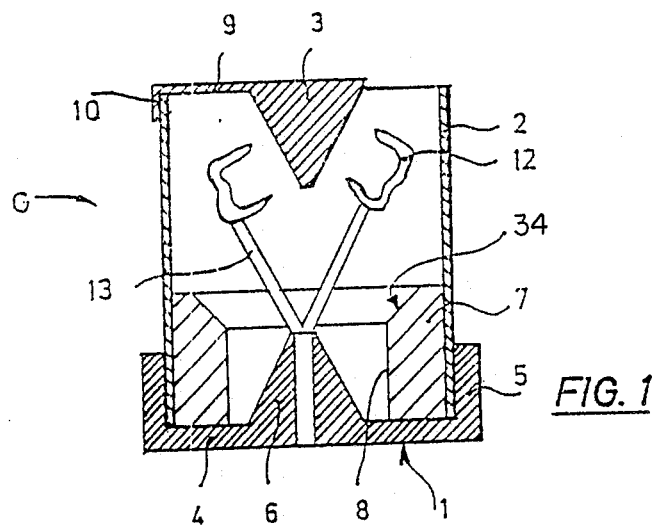
FIG. 1 shows a first embodiment of a casting mold in cross-section.

In the following, the first embodiment of a casting mold G is described with reference to FIG. 1. The casting mold G shown in FIG. 1 essentially consists of three main components, a funnel shaper 1 provided as a base, a muffle ring 2 and a blind funnel 3 opposite the funnel shaper. The funnel shaper has a disk-shaped base plate 4, at the circumference of which runs a wide wall 5 which stands vertical to the base plate 4. In the center of the base plate 4, a cone 6 is arranged, which forms a funnel for later pouring the metal melt into the solidified embedding mass. At the tip of the cone 6, the casting channels 13 of the wax model are attached. The pipe-shaped muffle ring 2 is partially inserted into this funnel shaper, i.e. with one end section, with the outside wall of the muffle ring 2 resting against the inside circumference of the side wall 5 of the funnel shaper 1 and sealing it. An air-tight seal between the funnel shaper 1 and the muffle ring 2 ensures that no air is drawn in during embedding, which might result in bubble formation in the casting object.

As is further evident from FIG. 1, the blind funnel 3 is arranged at the end of the muffle ring 2 opposite the funnel shaper 1, facing towards the cone 6 of the funnel shaper 1, with the tip of the blind funnel 3 and the tip of the cone 6 of the funnel shaper 1 facing one another.

Figure 2:
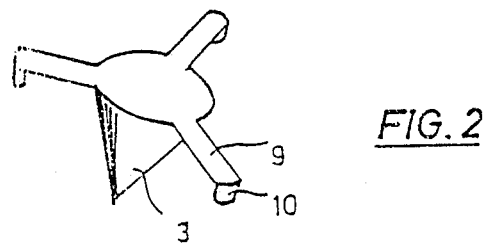
FIG. 2 shows the blind funnel in a perspective view.

As is evident from FIG. 2, the blind funnel is attached by means of supporting arms 9, whose free ends are bent at an angle 10 and which overlap the edge of the muffle ring 2. There is sufficient space between the supporting arms to allow the embedding mass to be filled in.

On the side of the muffle ring 2 which faces the funnel shaper 1, a cylindrical ring 7 is inserted flush with the bottom, the central opening 8 of which surrounds the cone 6 of the funnel shaper 1. The dimensions of this ring 7 and the blind funnel 3 are established in such a way, as a function of the arrangement of the casting objects, that later, approximately the same amount of embedding material will be found in the area of the casting objects. For this, it is advantageous to provide a bevel 34 on the inside wall of the ring 7 located on the interior of the muffle ring 2.

A suitable material for the ring 7 is an elastic material which simplifies removal of the ring 7 from the muffle ring 2 after the embedding mass has set. Alternatively, the ring 7 can be made of a wax which melts when the mold is preheated.

Figure 3:
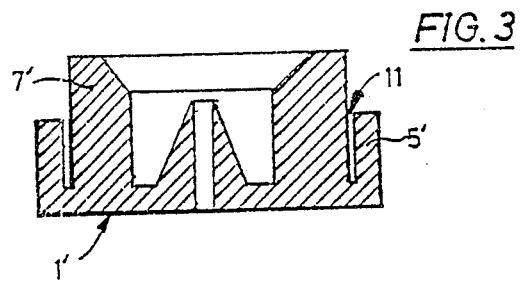
FIG. 3 shows a second embodiment of a casting mold, in which the funnel shaper and the ring are formed of one piece.

FIG. 3 shows the second embodiment of the casting mold, with only the casting funnel being shown. The other components of the casting mold correspond to those of the first embodiment. The funnel shaper 1' of the second embodiment differs from the first embodiment in that the ring 7' and the funnel shaper 1' form a unit, i.e. are made of one piece. For the purpose of air-tight insertion of the muffle ring 2 into the funnel shaper 1', a slit 11 is provided between the inside wall 5' and the outside wall of the ring 7', which holds the lower part of the muffle ring 2.

Figure 4:
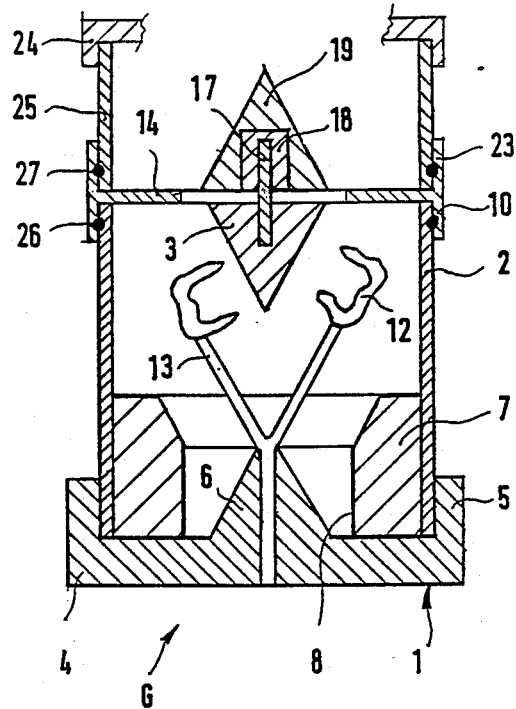
FIG. 4 shows an embodiment of a casting mold in cross-section, with a blind funnel which can be positioned as desired.
Figure 5:
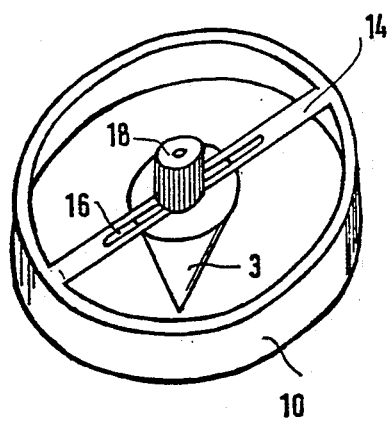
FIG. 5 shows the blind funnel with socket ring in a perspective view.

As is evident from FIG. 4 and 5, in another embodiment, the blind funnel 3 is attached to a stay 14, which in turn is attached at its ends to a socket ring 10 and passes through the center of the socket ring 10. This socket ring is placed on the upper edge of the muffle ring 2 and can be rotated relative to the muffle ring 2, to position the blind funnel, in the imaginary upper frontal surface of the muffle ring 2. The socket ring has a beveled edge in the direction of the center, so that it sits on the upper edge of the muffle ring 2 in a stable manner.

Figure 6:
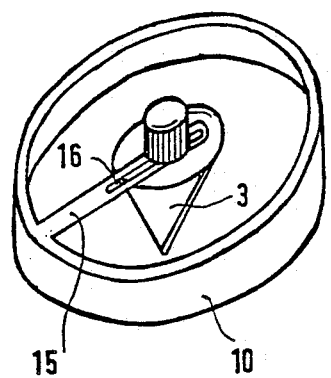
FIG. 6 shows another embodiment of a blind funnel with socket ring in a perspective view.
Figure 8:
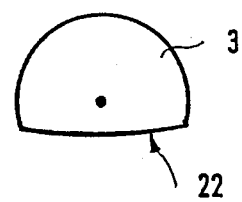
FIG. 8 shows another embodiment of a blind funnel.

As is evident from FIG. 6, a carrier 15 can also be provided in place of a stay 14, where this carrier is attached at one end to the socket ring 10 which overlaps the upper edge of the muffle ring 2, and whose other end extends to the center axis of the socket ring 10 in a radial direction.

The stay 14 and also the carrier 15 have a longitudinal slit 16, through which a threaded pin 17 projecting away from the bottom surface of the blind funnel 3 can pass, and is attached in such a way that it cannot rotate. A knurled nut 18 is screwed onto the threaded pin 17 passed through the longitudinal slit 16, which makes it possible to fix the blind funnel 3 at a pre-determined location of the carrier 15 or the stay 14.

Since the socket ring 10 can rotate relative to the muffler ring 2, and the blind funnel can be attached at a certain location of the carrier or stay, along the longitudinal slit 16, the blind funnel can therefore be positioned at a suitable location which is determined by the shape of the wax model and the distance to be maintained from it.

In order to prevent contamination of the knurled screw 18 and the longitudinal slit 16 when the embedding mass is poured into the muffle ring 2, a cover cone 19 is provided, which can be placed over the knurled screw 18. This cover cone 19 has a dead-end bore 22 in the center of its bottom surface, the contours of which correspond to the contours of the knurled screw. The diameter of the cover cone 19 is selected in such a way that the cover cone is seated securely after it is pressed onto the knurled screw. Once the knurled screw is contained within the cover cone, the bottom surface of the cover cone 19 and that of the blind funnel 3 face each other. Embedding mass which impacts against the slanted cone surface of the cover cone 19 when being poured into the muffle ring 12 is therefore guided into the muffle ring 2.

Figure 7:
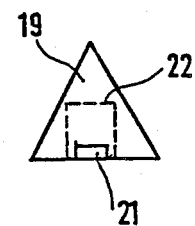
FIG. 7 shows the cover cone in a side view.

Since the casting mold G is placed on a shaker after the embedding mass has been introduced, in order to prevent bubble formation within the embedding mass, there is the danger, due to the vibrations caused by the shaker, that the knurled nut 18 will loosen and therefore the blind funnel 3 will shift. In order to preclude this, the cover cone 19 has a groove 21 in its bottom surface, as shown in FIG. 7, the contours of which essentially correspond to those of the stay 14 or the carrier 15. Before the cover cone 19 is pressed onto the knurled nut 18, the groove 21 is aligned relative to the carrier 15 or the stay 14. If the cover cone 19 is now pressed onto the nut 18, the carrier or stay comes to rest in the groove 21 in the final stage, and the bottom surfaces of the blind funnel 3 and the cover cone 19 come to rest against each other. In this way, loosening of the knurled nut 18 can be securely prevented.

In order to be able to use the casting mold described above also in combination with a vaccum stirrer pot, it is only necessary that a flange 23 be provided on the top of the socket ring 10, the outside diameter of which corresponds to that of the muffle ring 2. A conventional rubber cuff 24 can be placed on the on this flange 23, in order to produce a connection to the embedding mass outlet channel of the vacuum stirrer pot. Alternatively, the inside diameter of the ring-shaped flange 23 can correspond to the outside diameter of the muffle ring 2, so that a second metal ring 25 with a height adapted to the height of the cover cone 19 can be inserted into this flange (cf. FIG. 4). At the other frontal surface of the second metal ring 25, the rubber cuff 24 is then attached as described above. In order to achieve an air-tight seal between the rubber cuff 24, the metal ring 25 and the interior of the muffle ring 2, ring gaskets 26, 27 are arranged between the socket ring 10 and the outside wall of the muffle ring 2 as well as between the flange 23 and the metal ring 25.

As is evident from FIG. 7, the blind funnel 3 has a flattened area 22 on one side, i.e. the blind funnel 3 has a combination of curved and linear contours. If, for example, the wax model represents a linear bridge, it is placed opposite the flattened area 22 of the blind funnel 3, while a curved bridge is placed opposite the circular contours of the blind funnel. In this way, it can be assured, as a function of the shape of the wax model in each case, that later, approximately the same amount of embedding material is found in the area of the casting objects, which makes it possible to achieve high fitting accuracy of the casting objects.

While only a few embodiments of the present invention has been shown and described, it is to be understood that many changes and modifications may be made thereunto without departing from the spirit and scope of the invention.

I claim:

1. A dental casting mold for producing muffles for use in dental prosthetic manufacture comprising
   a base being a funnel shaper, having a circular base plate and a central cone and circumferential vertical side wall extending upwardly from the base plate;
   a cylindrical muffle ring inserted in the funnel shaper and having a base end thereof resting on the base plate and abutting an inner circumferential surface of the side wall;
   a cylindrical ring inserted on the side of the muffle ring facing the funnel shaper, the central opening of which ring surrounds the cone; and
   a blind funnel arranged at the end of the muffle ring opposite to the funnel shaper by a support said blind funnel consisting of a tapered funnel body tapering to a funnel tip, said funnel tip facing towards the cone of the funnel shaper;
   wherein the dimensions of said cylindrical ring and the blind funnel are established in such a way that approximately the same amount of embedding material is provided in the vertical, axial and transverse directions of the casting object mounted on the central cone of the base.

2. A casting mold according to claim 1, comprising a bevel on the inside wall of the ring which is located on the interior of the muffle ring.

3. A casting mold according to claim 1, wherein the ring is made of one piece with the funnel shaper and wherein a slit is provided between the inside circumference of the side wall of the funnel shaper and the outside circumference of the ring to hold the muffle ring.

4. A casting mold according to claim 1, wherein the ring is elastic.

5. A casting mold according to claim 1, wherein the ring is made of wax.

6. A casting mold according to claim 1, wherein the blind funnel is positioned and fixed in the frontal surface of the muffle ring.

7. A dental casting mold for producing muffles for use in dental prosthetic manufacture comprising
   a base being a funnel shaper, having a circular base plate and a central cone and circumferential vertical side wall extending upwardly from the base plate;
   a cylindrical muffle ring inserted in the funnel shaper and having a base end thereof resting on the base plate and abutting an inner circumferential surface of the side wall;
   a cylindrical ring inserted on the side of the muffle ring facing the funnel shaper, the central opening of which ring surrounds the cone; and
   a blind funnel arranged at the end of the muffle ring opposite to the funnel shaper and having a funnel tip facing towards the cone of the funnel shaper, said blind funnel having supporting arms which extend radially, the free ends of which are bent at an angle and overlap the edge of the muffle ring;
   wherein the dimensions of said cylindrical ring and the blind funnel are established in such a way that approximately the same amount of embedding material is provided in the vertical, axial and transverse directions of the casting object mounted on the central cone of the base.

8. A dental casting mold for producing muffles for use in dental prosthetic manufacture comprising
   a base being a funnel shaper, having a circular base plate and a central cone and circumferential vertical side wall extending upwardly from the base plate;
   a cylindrical muffle ring inserted in the funnel shaper and having a base end thereof resting on the base plate and abutting an inner circumferential surface of the side wall;
   a cylindrical ring inserted on the side of the muffle ring facing the funnel shaper, the central opening of which ring surrounds the cone; and
   a blind funnel arranged at the end of the muffle ring opposite to the funnel shaper and having a funnel tip facing towards the cone of the funnel shaper, said blind funnel being positioned and fixed along a stay which is attached at its ends to a socket ring which overlaps the upper edge of the muffle ring and is rotatable relative to it, and runs through the center of the socket ring;
   wherein the dimensions of said cylindrical ring and the blind funnel are established in such a way that approximately the same amount of embedding material is provided in the vertical, axial and transverse directions of the casting object mounted on the central cone of the base.

9. A casting mold according to claim 8, wherein the stay or the carrier has a longitudinal slit;
   wherein the blind funnel has a threaded pin projecting away from the bottom surface of the funnel, which runs in the direction of the funnel axis; and
   wherein the threaded pin which passes through the longitudinal slit, and a knurled nut is screwed onto the threaded pin.

10. A casting mold according to one of claim 9, wherein the stay or the carrier is attached to the socket ring in such a way that it can be replaced.

11. A casting mold according to claim 9, wherein a cover cone is provided, the bottom surface of which essentially corresponds to that of the blind funnel, that a dead-end bore is provided in the center of the bottom surface, running towards the cone tip, and that the diameter and the length of the dead-end bore correspond to the diameter and the length of the knurled nut.

12. A casting mold according to claim 11, wherein in the bottom surface of the cover cone, a groove running through the center of the bottom surface is provided, the contours of which correspond to those of the carrier.

13. A casting mold according to one of claim 12, wherein the blind funnel has a flattened area on one side.

14. A casting mold according to one of claim 8, wherein a ring-shaped flange is arranged on the side of the socket ring which faces away from the muffle ring, the outside diameter of which corresponds to that of the muffle ring.

15. A casting mold according to claim 14, wherein a ring gasket is placed between the socket ring and the outside wall of the muffle ring, which is connected with a vacuum stirrer pot by a rubber cuff.

16. A casting mold according to claim 14, wherein a ring gasket is placed between the flange and the metal ring, which is connected with a vacuum stirrer pot by a rubber cuff.

17. A dental casting mold for producing muffles for use in dental prosthetic manufacture comprising a base being a funnel shaper, having a circular base plate and a central cone and circumferential vertical side wall extending upwardly from the base plate;

a cylindrical muffle ring inserted in the funnel shaper and having a base end thereof resting on the base plate and abutting an inner circumferential surface of the side wall;

a cylindrical ring inserted on the side of the muffle ring facing the funnel shaper, the central opening of which ring surrounds the cone; and a blind funnel arranged at the end of the muffle ring opposite to the funnel shaper and having a funnel tip facing towards the cone of the funnel shaper, said blind funnel being positioned and fixed along a carrier which is attached at one end to a socket ring which overlaps the upper edge of the muffle ring and is rotatable relative to it, and whose other end extends to the center axis of the socket ring in a radial direction;

wherein the dimensions of said cylindrical ring and the blind funnel are established in such a way that approximately the same amount of embedding material is provided in the vertical, axial and transverse directions of the casting object mounted on the central cone of the base.

* * * * *